(12) United States Patent
Bouvier et al.

(10) Patent No.: US 9,101,318 B2
(45) Date of Patent: Aug. 11, 2015

(54) X-RAY MEDICAL APPARATUS FURNISHED WITH LUMINOUS DEVICES CONTROLLED AS A FUNCTION OF THE MODE OF OPERATION OF THE APPARATUS

(71) Applicant: General Electric Company, Schenectady, NY (US)

(72) Inventors: Bernard Bouvier, Buc (FR); Jean-Michel Marteau, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 284 days.

(21) Appl. No.: 13/680,451

(22) Filed: Nov. 19, 2012

(65) Prior Publication Data

US 2013/0136232 A1    May 30, 2013

(30) Foreign Application Priority Data

Nov. 24, 2011 (FR) ...................................... 11 60763

(51) Int. Cl.
*A61B 6/00* (2006.01)
*H05G 1/54* (2006.01)

(52) U.S. Cl.
CPC . *A61B 6/44* (2013.01); *A61B 6/462* (2013.01); *A61B 6/4435* (2013.01); *A61B 6/504* (2013.01)

(58) Field of Classification Search
USPC ............................... 378/91, 98, 114, 115, 116
See application file for complete search history.

(56) References Cited

U.S. PATENT DOCUMENTS

| 6,144,876 | A | 11/2000 | Bouton |
| 7,502,444 | B2 | 3/2009 | Marar |
| 2003/0198317 | A1 | 10/2003 | Nakagawa et al. |
| 2010/0296632 | A1 | 11/2010 | Bouvier |
| 2011/0122995 | A1 | 5/2011 | Ferro, Jr. |

OTHER PUBLICATIONS

Search Report and Written Opinion from corresponding French application No. 1160763, dated Jul. 30, 2012.

*Primary Examiner* — Nicole Ippolito
*Assistant Examiner* — Hanway Chang
(74) *Attorney, Agent, or Firm* — GE Global Patent Operation; Marc A. Vivenzio

(57) ABSTRACT

An X-ray apparatus is provided. The X-ray apparatus comprises: an X-ray tube; an X-ray detector disposed opposite the X-ray tube in a direction of the emission of X-rays; and a set of luminous devices controlled by a central unit controlling the operation of the apparatus so as to emit luminous radiations as a function of the mode of operation of the apparatus.

14 Claims, 4 Drawing Sheets

X-RAY MEDICAL APPARATUS FURNISHED WITH LUMINOUS DEVICES CONTROLLED AS A FUNCTION OF THE MODE OF OPERATION OF THE APPARATUS

BACKGROUND OF THE INVENTION

Embodiments of the invention generally relate, to X-ray apparatuses used in the field of medical imaging. More particularly, embodiments of the invention pertain to the formulation and restitution of information conveying the mode of operation of the apparatus.

X-ray medical apparatuses are used in angiographic examinations for diagnostic or interventional purposes. They conventionally comprise an X-ray tube and an X-ray detector disposed opposite the X-ray tube in a direction of emission of the X-rays. The tube and the detector are generally placed at two mutually opposite ends of an arm, the arm articulated on a body.

During the examination phases, radiographs of a region of interest of the body of a patient need to be carried out via X-rays. After the patient lies down on an examination table, the X-ray tube and the detector are arranged so as to face the zone to be radiographed.

X-ray apparatuses are known, for example, to be fixed to the floor in which the arm supporting the X-ray tube and the detector comprise several degrees of freedom making it possible to position the X-ray beam facing the region of interest.

However, the requirement in radiography is necessary at only the start and the end of the examination. During the time in between, access to the patient must be favored. Being fixed to the floor, the apparatus may not be sited away from the examination table when not being used. In particular, the transfer and the installation of the patient on the examination table are impeded by the presence of this bulky system.

Moreover, manually movable so-called "surgical mobile" X-ray apparatuses exist. They are in this case mounted on a trolley wherein a certain number of batteries supply energy to the X-ray tube. This type of apparatus is not suitable for angiographic examinations in so far as the power delivered by the X-ray tube is no longer sufficient to obtain sufficient image quality and, in particular, contrast.

Furthermore, the mobile X-ray apparatus does not allow complex angulations since the diameter of the arm supporting the tube and the detector is not sufficiently great. Likewise, these mobile X-ray apparatuses do not make it possible to obtain a speed of rotation of the arm which is sufficient to allow good quality three-dimensional image reconstructions. Finally, even though the weight of such an apparatus is half that of an X-ray apparatus intended for angiography, the mobile X-ray apparatus remains very difficult to move because of relatively large dimensions and a weight of up to 300 kg.

Therefore, an X-ray apparatus is provided, the body of the X-ray apparatus comprising a mobile device furnished with wheels driven by drive motors and controlled in an automatic manner under the command of a navigation system. In this regard, reference may be had to document FR 2 945 724.

With respect to positioning, a system is particularly effective if the X-ray tube and the detector may be positioned around the reuion of interest and may be sited elsewhere when it is no longer being used, so as to free the space around the examination table.

It is desirable, however, to be able to directly assess the mode of operation of the apparatus and the type of action instigated by the mobile device so as to, for example, immediately identify the implementation of phases of forward movement, rearward clearance, rotation, etc.

Generally, it is also desirable to be able to directly identify the mode of operation of the apparatus independent of the type of X-ray apparatus used: fixed, surgical mobile, or automatic movement type.

BRIEF DESCRIPTION OF THE INVENTION

According to an embodiment of the present invention, an X-ray medical apparatus is provided. The apparatus comprises an X-ray tube; an X-ray detector disposed opposite the X-ray tube in a direction of the emission of X-rays; a set of luminous devices; and a central unit configured to control the set of luminous devices to emit luminous radiations as a function of modes of operation of the apparatus.

BRIEF DESCRIPTION OF THE DRAWINGS

Other aims, characteristics and advantages of the invention will be apparent on reading the following description, given solely by way of non-limiting example and with reference to the appended drawings, in which.

DETAILED DESCRIPTION OF THE INVENTION

Figure 1:
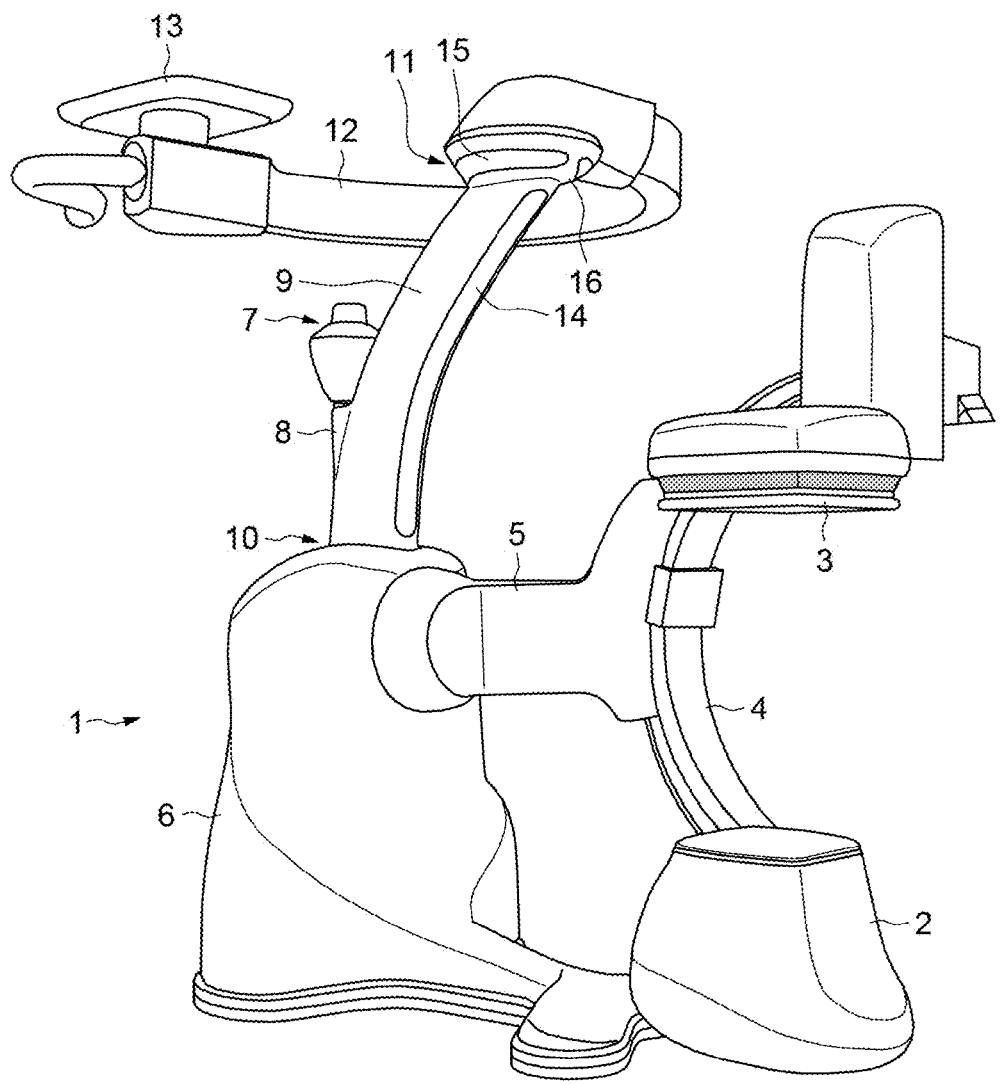
FIG. 1 is a view of a mobile X-ray apparatus equipped with luminous devices in accordance with an embodiment of the present invention.

FIG. 1 illustrates an X-ray apparatus of vascular type, designated by the general numerical reference 1.

The apparatus 1 comprises: an X-ray tube 2 able to emit an X-ray beam along a direction of emission; and an X-ray detector 3, wherein the X-ray tube and X-ray detector are disposed at the two mutually opposite ends of an arm 4, for example, in the form of a cradle, so that the X-rays emitted by the tube 2 are incident on the detector 3.

During radiography, the tube 2 and the detector 3 are brought facing a region of interest of the body of a patient lying down on an examination table so that, when the region of interest is interposed between the X-ray tube 2 and the detector 3, it is irradiated by the X-rays and the detector 3 produces data representative of characteristics of the interposed region of interest.

The arm 4 is mounted in a sliding manner on a second arm 5 mounted in a rotatable manner with respect to a fixed body 6.

Thus, the body 6, the rotatable arm 5, and the arm 4 are all articulated with respect to one another so that the X-ray apparatus can move in three dimensions and produce images of an organ to be examined at various angles of incidence.

According to an embodiment of the present invention, the body 6 of the apparatus comprises a mobile device controlled in an automatic manner. It would not be a departure from the framework of the invention, however, should the apparatus be fixed or of the "surgical mobile" type.

The mobile device comprises, for example, a roller system comprising two motive and steerable lateral wheels placed at the rear, and two free front wheels, the motive wheels being associated with drive means comprising a steering motor coupled to a drive motor. The mobile device may be a programmable device and may be associated with a navigation system capable for example of cooperating with locating elements placed in the operating room so as to allow the apparatus to be precisely located in the room as well as with respect to the examination table.

For example, the navigation system may be based upon the use of a laser emitter/receiver 7 placed at the upper end of an arm 8 erected from the body 6, as well as a set of targets disposed regularly on the peripheral walls of the operating room so as to precisely locate the apparatus by telemetry in the operating room on the basis of the laser rays emitted by the emitter/receiver 7, reflected by the targets, and detected by a sensor associated with the emitter/receiver 7. Other locating systems may also be used.

The apparatus 1 is connected to remote cabinets situated in technical premises by a set of connection elements. These connection elements comprise: a set of power and electrical connection cables dedicated to supplying the apparatus with electrical energy, conduits in which a cooling fluid circulates, the cooling fluid being, for example, water; and data transmission channels of an optical fiber type.

The body 6 of the apparatus comprises a substantially curved mast 9, in which the connection elements run, the mast having a lower end 10 mounted on the body 6 and an upper end 11, wherein a first end of a support device 12 for the connection elements is pivotably mounted to the upper end 11, and wherein another end of the support device 12 is pivotably fixed on a plinth 13, the plinth fixed to the ceiling. For example, the support device 12 is formed by an association of articulated links capable of confining the bundle of connection elements in a horizontal plane situated in the area of the ceiling of the operating or examination room.

The X-ray apparatus 1 illustrated in FIG. 1 constitutes an automatic apparatus capable of implementing phases of examination and phases of movement under the command of a central processing unit placed in the body 6 of the apparatus or sited remotely, and possibly under the command of, control handles provided on a remote desk that can be manipulated by an operator.

With respect to FIG. 1, the X-ray apparatus 1 further comprises luminous devices 14 and 15 configured to provide the operators in the operating room with information conveying the mode of operation of the apparatus. According to another embodiment, the luminous devices are configured to provide lighting or a luminous ambiance conferring an aesthetic aspect on the apparatus as well as to make it possible to identify the range to which the apparatus belongs.

According to the embodiment illustrated in FIG. 1, the apparatus 1 comprises two luminous devices, wherein a first luminous device is arranged along the mast 9 and a second luminous device is arranged on a saucer 16 at the upper end 11 of the mast 9 on which the support device 12 is mounted.

Figure 2:
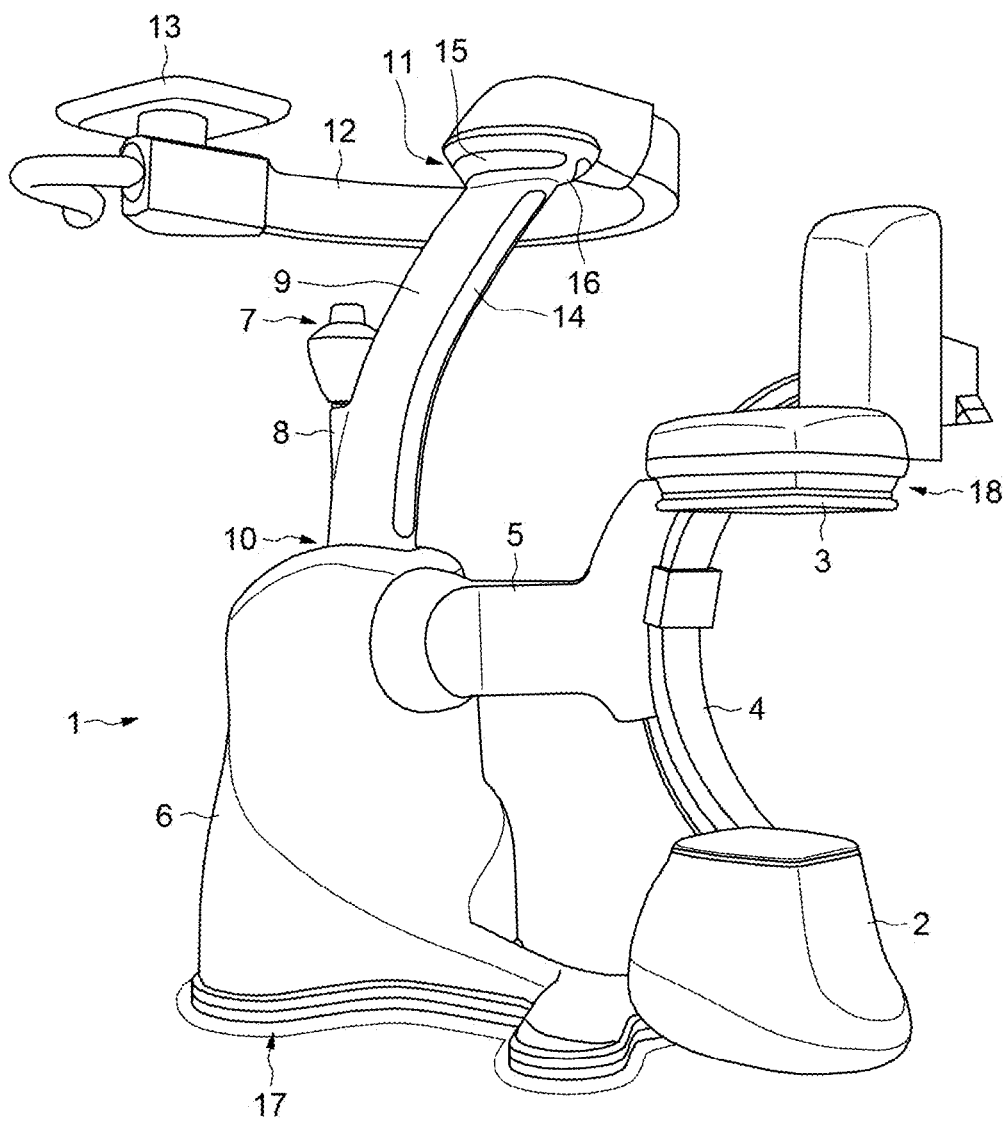
FIG. 2 illustrates an X-ray apparatus in accordance with an embodiment of the present invention.

According to the embodiment illustrated in FIG. 2, the apparatus further comprises a third luminous device 17 provided at the base of the body 6 and pointing in the direction of the floor so as to engender a localized lighting zone on the floor. According to another embodiment, the apparatus further comprises a fourth luminous device 18 provided on the framework of the detector 3.

According to various embodiments, the luminous devices are controlled by the central processing unit placed for example in the body 6 according to programmed phases of light emission previously stored in memory. Each of the programmed phases is associated with a mode of operation of the apparatus so as to bring about the emission of a luminous radiation conveying the mode of operation of the apparatus or to provide localized or ambient lighting.

The programmed modes, for example, may provide luminous indications to show that the apparatus is in operation, to indicate the operative mode in progress, or to indicate a degraded mode of operation, as well as locally illuminate the operating room. Furthermore, the programmed modes may entail conferring a particular luminous ambiance or improving the aesthetic aspect of the apparatus.

The second luminous device 15 provided on the saucer 16, for example, may be configured to emit a fixed luminous signal when the apparatus is operating, a luminous signal in the form of beats when the apparatus is moving, or a colored luminous signal, for example, yellow, blue, pink or green, when the apparatus is in a degraded mode, corresponding to a safety alarm.

The second luminous device 15 provided on the saucer 16 is able to emit light over a span of substantially 360° and is thus visible from anywhere in the operating room. When the light is white, the light contributes to the luminous and aesthetic ambiance of the apparatus as a whole.

The first luminous device 14, which extends along the entire length of the mast 9, is produced in the form of a luminous strip which extends along a sector of the mast and points in the direction of the patient. The first luminous device is configured to provide a luminous ambiance to the apparatus, jointly with the light emitted by the second luminous device 15 during the normal operation of the apparatus, in the form of monochrome lighting, for example, a white light or in the form of a luminous beat.

The fourth luminous device provided on the detector is configured to provide lighting of the zone of the patient on the examination table as well as a luminous ambiance harmonized with the apparatus as a whole.

The third luminous device 17, pointing towards the floor, also improves the general aesthetic aspect of the lighting provided by the apparatus. But the third luminous device 17 may furthermore be used to give indications relating to the direction of movement of the apparatus. Moreover, the third luminous device 17 may be provided over the entire periphery of the base of the body of the apparatus and be locally illuminated on the side corresponding to a direction of movement of the apparatus.

According to the various embodiments, the luminous devices are produced in the form of an array of light-emitting diodes comprising at least two pairs of strips of diodes placed side by side and offset from one another so as to afford homogeneous lighting. According to another embodiment, at least three diodes are provided every 5 cm.

Figure 3:
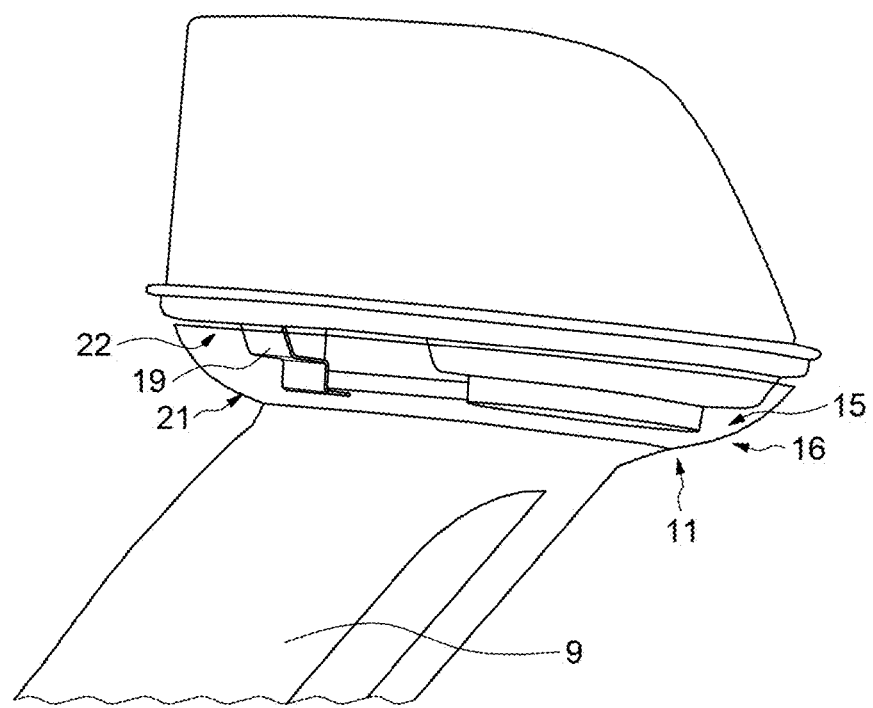
FIG. 3 is a detailed view of the upper end of the mast of the apparatus of FIGS. 1 and 2.
Figure 4:
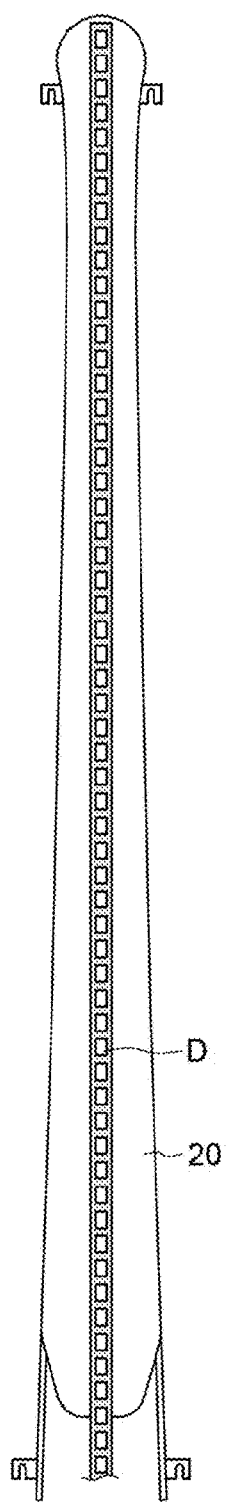
FIG. 4 is a detailed view of a luminous device configured to be provided on the mast of the apparatus of FIGS. 1 and 2.

Referring to FIGS. 3 and 4, which illustrate the mounting of an array of light-emitting diodes on the saucer 16 and on the mast 9, respectively, the light-emitting diodes D are mounted on a metallic reflector 19 and 20 and are shrouded by a diffuser 21.

With respect to the mounting of the diodes on the saucer, illustrated in FIG. 3, the diodes are mounted on a horizontal annular reflector while the diffuser 21 extends at an angle of about 45° with respect to the direction of emission of the light rays.

A distance between the diodes D and the constituent material of the diffuser, as well as an appropriate thickness of the diffuser is provided so as to obtain a homogeneous light and a good yield of quality. For example, Plexiglas® is provided, the exterior and interior surfaces furnished with a sand-blasted finish so as to mask the diodes when the devices are unlit and to obtain a dull light when the devices are lit. According to another embodiment, a sand-blasted finish may be provided on just one of either the interior surface or exterior surface.

According to another embodiment, the second luminous device 15 comprises a hood 22 produced in the form of an annular dish capable of avoiding the projection of light onto the ceiling.

According to another embodiment, a seal is provided. The seal is opaque to light and is configured to be inserted between the diffuser and the constituent material of the body 6, including the mast 9, so as to avoid leakages of light.

As previously indicated, the light-emitting diodes D used for the production of the luminous devices are produced in the form of a strip of multicolor diodes. When the devices are produced on the basis of several parallel strips of diodes, the strips have different orientations. The adjustment of the diodes may be carried out after the mounting of the whole set of diodes and in a separate manner for each of the luminous devices.

According to another embodiment of the present invention, the central unit comprises a set of programmed modes of light emission stored in memory, wherein each of the programmed modes is associated with a mode of operation of the apparatus.

According to another embodiment, the luminous devices comprise luminous sources of variable colors. According to yet another embodiment, the luminous devices comprise luminous sources able to emit light in the form of beats.

According to an embodiment of the present invention, the luminous devices comprise an array of light-emitting diodes. According to yet another embodiment, the array comprises at least three light-emitting diodes every 5 cm.

According to an embodiment of the present invention, the luminous devices comprise at least two pairs of parallel strips of diodes, said strips being offset so that a diode of one of the strips is inserted between the two diodes of the other strip.

According to another embodiment, each of the luminous devices comprise: a reflector on which are mounted the diodes; and a diffuser of the light, the diffuser shrouding the said diodes and having a sand-blasting on at least one of either an internal surface of the diffuser or an external surface of the diffuser.

According to another embodiment of the present invention, each of the luminous devices is configured for a light-tight seal arranged between the diffuser and the body of the apparatus.

According to another embodiment, the body of the apparatus is furnished with a mast erected for the passage of connection elements of the apparatus, the mast comprising: a first luminous device over at least one part of the length of the mast; and a second luminous device arranged on an upper end saucer of the mast.

According to another embodiment of the present invention, a third luminous device is provided. The third luminous device is directed downwards and placed at the base of the apparatus.

According to yet another embodiment of the present invention, a fourth luminous device is provided. The fourth luminous device is placed on the framework of the X-ray detector.

What is claimed is:

1. An X-ray medical apparatus comprising:
   an X-ray tube;
   an X-ray detector disposed opposite the X-ray tube in a direction of the emission of X-rays;
   a set of luminous devices;
   a mast defining a passage for connection elements, the mast comprising at least one luminous device of the set of luminous devices, which is arranged over at least a part of the length of the mast; and
   a central unit configured to control the set of luminous devices to emit luminous radiations as a function of modes of operation of the apparatus.

2. The apparatus according to claim 1, wherein the central unit comprises a set of programmed modes of light emission, wherein each of the programmed modes is associated with a mode of operation of the apparatus.

3. The apparatus according to claim 1, wherein the luminous devices comprise luminous sources of variable colors.

4. The apparatus according to claim 1, wherein the luminous devices comprise luminous sources configured to emit light in the form of beats.

5. The apparatus according to claim 1, wherein the luminous devices comprise an array of light-emitting diodes.

6. The apparatus according to claim 5, wherein the array of light-emitting diodes comprises at least three light-emitting diodes every 5 cm.

7. The apparatus according to claim 5, wherein the luminous devices comprise at least two pairs of parallel strips of diodes, and wherein the strips are offset so that a diode of one of the at least two strips is inserted between two diodes of another of the two strips.

8. The apparatus according to claim 5, wherein the luminous devices comprise:
   a reflector on which the diodes are mounted; and
   a diffuser configured to shroud the diodes and having a sand-blasting on at least one of an internal surface of the diffuser and an external surface of the diffuser.

9. The apparatus according to claim 8, wherein the luminous devices comprise a light-tight seal arranged between the diffuser and a body of the apparatus.

10. An X-ray medical apparatus comprising:
    an X-ray tube;
    an X-ray detector disposed opposite the X-ray tube in a direction of the emission of X-rays;
    a mast defining a passage for connection elements;
    an end saucer located at an upper end of the mast;
    a set of luminous devices comprising at least a first luminous device arranged over at least a part of the length of the mast and a second luminous device is arranged on the end saucer; and
    a central unit configured to control the set of luminous devices to emit luminous radiations as a function of modes of operation of the apparatus.

11. The apparatus according to claim 10, wherein a base of the apparatus comprises a third luminous device.

12. The apparatus according to claim 11, further comprising a fourth luminous device arranged on a framework of the X-ray detector.

13. An X-ray medical apparatus comprising:
    an X-ray tube;
    an X-ray detector disposed opposite the X-ray tube in a direction of the emission of X-rays;
    a set of luminous devices; and
    a central unit configured to control the set of luminous devices to emit luminous radiations as a function of modes of operation of the apparatus,
    wherein the luminous devices comprise an array of light-emitting diodes comprising at least two pairs of parallel strips of diodes that are offset so that a diode of one of the at least two strips is inserted between two diodes of another of the two strips.

14. The apparatus according to claim 10, wherein the luminous devices comprise an array of light-emitting diodes comprising at least two pairs of parallel strips of diodes that are offset so that a diode of one of the at least two strips is inserted between two diodes of another of the two strips.

* * * * *

UNITED STATES PATENT AND TRADEMARK OFFICE
CERTIFICATE OF CORRECTION

| | | |
|---|---|---|
| PATENT NO. | : 9,101,318 B2 | Page 1 of 1 |
| APPLICATION NO. | : 13/680451 | |
| DATED | : August 11, 2015 | |
| INVENTOR(S) | : Bouvier et al. | |

It is certified that error appears in the above-identified patent and that said Letters Patent is hereby corrected as shown below:

In the Specification

In Column 1, Line 62, delete "reuion" and insert -- region --, therefor.

Signed and Sealed this
Twelfth Day of January, 2016

Michelle K. Lee
*Director of the United States Patent and Trademark Office*